United States Patent
Rosowsky et al.

(10) Patent No.: US 6,989,386 B2
(45) Date of Patent: Jan. 24, 2006

(54) PHARMACEUTICALLY ACTIVE ORNITHINE DERIVATIVES, AMMONIUM SALTS THEREOF AND METHODS OF MAKING SAME

(75) Inventors: Andre Rosowsky, Needham, MA (US); Henry Bader, Canton, MA (US); Peter Blumbergs, Royal Oak, MI (US); Ming-The Lin, Farmington Hills, MI (US)

(73) Assignees: Dana-Farber Cancer Institute, Boston, MA (US); Ash Stevens, Inc., Detroit, MI (US)

( * ) Notice: Subject to any disclaimer, the term of this patent is extended or adjusted under 35 U.S.C. 154(b) by 18 days.

(21) Appl. No.: 10/412,279

(22) Filed: Apr. 14, 2003

(65) Prior Publication Data

US 2004/0072837 A1 Apr. 15, 2004

Related U.S. Application Data

(60) Provisional application No. 60/376,615, filed on Apr. 30, 2002.

(51) Int. Cl.
*C07D 475/08* (2006.01)
*A61K 31/519* (2006.01)
*A61P 35/02* (2006.01)

(52) U.S. Cl. ................... 514/262.1; 544/260

(58) Field of Classification Search ............... 544/260; 514/262.1

See application file for complete search history.

(56) References Cited

U.S. PATENT DOCUMENTS

| 4,767,761 A | 8/1988 | Rosowsky | 514/249 |
| 4,956,461 A | 9/1990 | Rosowsky | 544/258 |
| 2002/0103212 A1 | 8/2002 | Serizawa et al. | |

FOREIGN PATENT DOCUMENTS

WO    PCT/US04/005356    8/2004

OTHER PUBLICATIONS

Draetta, G. and Pagano, M. in "Annual Reports in Medicinal Chemistry, vol. 31", 1996, Academic Press, San Diego, p 241–248.*
Chen G. et al., "Dihydrofolate Reductase Binding and Cellular Uptake of Nonpolyglutamatable Antifolates: Correlates of Cytotoxicity Toward Methotrexate–Sensitive and –Resistant Human Head and Neck Squamous Carcinoma Cells," Molecular Pharmacology, 48:758–765 (1995).
Freisheim J.H. et al., "Photoaffinity Analogues of Methotrexate as Folate Antagonist Binding Probes," Adv. Enzyme Regul. 37, p. 15–27.
Holden, S.A. et al:, "Antifolates can potentiate topoisomerase II inhibitors in vitro and in vivo," Cancer Chemotherapy Pharmacology, 36:165–171, 1995.
Kempton, R. et al., Proc. Int. Symp. Pteredines Folic Acid Deriv., 8th, p. 671–674, 1988.
Mauritz, R., et al., Proceed. of the Int. Symp. On Pteredines and Folates 11th, p. 157–162.
Piper, J.R. et al., "Syntheses and Evaluation as Antifolates of MTX Analogues Derived From 2,ω–Diaminoalkanoic Acids,"J. Med. Chem., 28:1016–1025, 1985.
Price, E.M. et al., "Photoaffinity Analogues of Methotrexate as Probes for Dihydrofolate Reductase Structure and Function," Biochemical Pharmacology, 35(23):4341–4343, 1986.

(Continued)

*Primary Examiner*—Thomas C. McKenzie
(74) *Attorney, Agent, or Firm*—Jones Day

(57) ABSTRACT

In one embodiment, the present invention relates to a new class of ammonium salts of $N^\delta$-acyl derivatives of $N^\alpha$-(4-amino-4-deoxypteroyl)-L-ornithine compounds having a structure according to formula II–IV.

Formula II has the structure of:

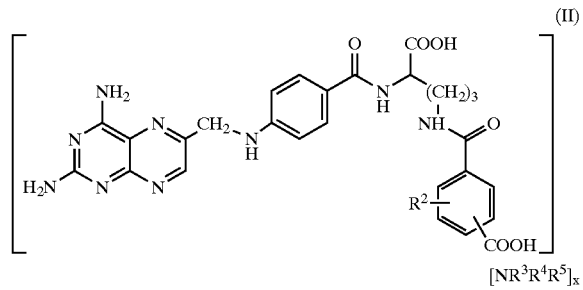

wherein:
$R^2$ represents up to four groups independently selected at each occurrence of $R^2$ from the group consisting of hydrogen, $C_{1-6}$ alkyl, $C_{2-6}$ alkenyl, $C_{2-6}$ alkynyl, $C_{3-8}$ cycloalkyl, $C_{1-6}$ alkoxy, chloro, fluoro, hydroxy, and —COOH;

$R^3$, $R^4$, and $R^5$ are each independently selected from hydrogen and $C_{1-6}$ alkyl; or $NR^3R^4$ taken combination can form a 5 to 7 member heterocycle having at least one nitrogen ring atom; and x is a real number greater than 0 and less than about 4.

The ammonium salts provided by the invention exhibit high inhibitory activity against the growth o methotrexate-resistant cells, and also exhibit superior chemical stability than corresponding acidic $N^\delta$-acyl derivatives of $N^\delta$-acyl derivatives of $N^\alpha$(4-amino-4-deoxypteroyl)-L-ornithine compounds.

68 Claims, No Drawings

OTHER PUBLICATIONS

Price, E.M. et al., "Photoaffinity Analogues of Methotrexate as Folate Antagonist Binding Probes. 1. Photoaffinity Labeling of Murine L1210 Dihydrofolate Reductase and Amino Acid Sequences of the Binding Region," Biochemistry 26:4751–4756, 1987.

Price, E.M. et al., "Photoaffinity Analogues of Methotrexate as Folate Antagonist Binding Probes. 2. Transport Studies, Photoaffinity Labeling, and Identification of the Membrane Carrier Protein for Methotrexate from Murine L1210 Cells," Biochemistry, 26:4757–4763, 1987.

Rhee, M.S., et al., "Effect of a Novel Antifolate, $N^{\alpha}$–(4–Amino–4–Deoxypteroyl)–$N^{\delta}$ – Hemiphthaloyl – L– Ornithine (PT523), on Growth of H35 Rat Hepatoma and HEPG2 Human Hepatoma Cells," Advances in Exper. Med & Biology, 338:461–464, 1993.

Rhee, M.S., et al., "Biochemical Studies on PT523, a Potent Nonpolyglutamatable Antifolate, in Cultured Cells," Molecular Pharmacology, 45:783–791, 1994.

Rosowsky, A. et al., "Methotrexate Analogues. 26. Inhibition of Dihydrofolate Reductase and Folylpolyglutamate Synthetase Activity and in Vitro Tumor Cell Growth by Methotrexate and Aminopterin Analogues Containing a Basic Amino Acid Side Chain," J. Med. Chem. 29:655–660, 1986.

Rosowsky, A. et al., "Methotrexate Analogues. 33. $N^{\delta}$–Acyl– $N^{\alpha}$–(4–amino–4–deoxypteroyl)–L–ornithine Derivatives: Synthesis and in Vitro Antitumor Activity," J. Med. Chem. 31:1332–1337, 1988.

Rosowsky, A. et al., "Synthesis of the Folylpolyglutamate Synthetase Inhibitor $N^{\alpha}$–Benzoyl and $N^{\delta}$–Hemiphthaloyl Derivatives, and an Improved Synthesis of $N^{\alpha}$–(4–Amino–4–deoxypteroyl)– $N^{\delta}$–hemiphthaloyl–L–ornithine," Pteridines, 1:91–98, 1989.

Rosowsky, A. et al., "Influence of Lipophilicity and Carboxyl Group Content on the Rate of Hydroxylation of Methotrexate Derivatives By Aldehyde Oxidase," Biochemical Pharmacology, 40(4):851–857, 1990.

Rosowsky, A. et al., "Synthesis and Biological Activity of Methotrexate Analogues with Two ACid Groups and a Hydrophobic Aromatic Ring in the Side Chain," J. Med. Chem . . . 34:574–579, 1991.

Rosowsky, A. et al., "Semisynthesis and Biological Activity of $N^{\omega}$–Hemiphthaloyl–α,ω–diaminoalkanoic Acid Analogues of Aminopterin and 3',5–Dichloroaminopterin," J. Med. Chem. 37:2167–2174, 1994.

Westerhof, G.R. et al., "Carrier– and Receptor–Mediated Transport of Folate Antagonists Targeting Folate–Dependent Enzymes: Correlates of Molecular–Structure and Biological Activity," Molecular Pharmacology, 48:459–471, 1995.

Wright, J.E. et al., "Pharmacokinetics, antifolate activity and tissue distribution of PT523 in SCC VII tumor–bearing mice," Cancer Chemother. Pharmacol. 42:300–306, 1998.

Rosowsky, et al. 1988, "Methotrexate Analogues. 33. $N^{\delta}$–Acyl–$N^{\alpha}$(4–amino–4–deoxypteroyl)–L–Ornithine Derivatives: Synthesis and in Vitro Antitumor activity" J. Med. Chem. 31: 1332–1337.

Rosowsky, et al. 1998, "Synthesis and Potent Antifolate Activity and Cytotoxicity of B–Ring Deaza Analogues of the Nonpolyglutamatable Dihydrofolate Reductase Inhibitor $N^{\alpha}$–(4–amino–4–deoxypteroyl) $N^{67}$–hemiphthaloyl–L–Ornithine (PT523)" J. Med. Chem. 41: 5310–5319.

Rosowsky, et al. 2000, "The Effect of Side–Chain. Para–aminobenzoyl region, B–Ring Modifications on Dihydrofolate Reductase Binding, Influx via the Reduced Folate Carrier, and Cytotoxicity of the Potent Nonpolyglutamatable Antifolate $N^{\alpha}$–(4–amino–4–deoxypteroyl) $N^{67}$ –hemiphthaloyl–L–Ornithine" Pharmacology & Therapeutics, 85:191–205.

Vaidya, et al, 2002, "Synthesis and In Vitro Antitumor Activity of New Deaza Analogues of the Nonpolyglutamatable Antifolate $N^{\alpha}$–(4–Amino–4–deoxypteroyl)–$N^{\delta}$ – Hemiphthaloyl – L – Ornithine (PT523)", J. Med Chem. 45: 1690–1696.

* cited by examiner

PHARMACEUTICALLY ACTIVE ORNITHINE DERIVATIVES, AMMONIUM SALTS THEREOF AND METHODS OF MAKING SAME

CROSS REFERENCE TO RELATED APPLICATIONS

This application claims the benefit of U.S. provisional application No. 60/376,615, filed Apr. 30, 2002, the content of which is incorporated herein by reference in its entirety.

This invention was made with government support under Grant RO1-CA25394 from the National Cancer Institute of the National Institutes of Health. The government has certain rights in the invention.

BACKGROUND OF THE INVENTION

1. Field of the Invention

The present invention provides pharmaceutically active ornithine compounds, particularly to pharmaceutically acceptable ammonium salts of $N^\delta$-acyl derivatives of $N^\alpha$-(4-amino-4-deoxypteroyl)-L-ornithine compounds. Preferred ammonium salts of the invention have superior chemical stability than corresponding free acid formulations.

2. Background $N^{\alpha\text{-}}$(4-amino-4-deoxypteroyl)-L-ornithine ("APA-L-Orn") has a structure according to Formula I:

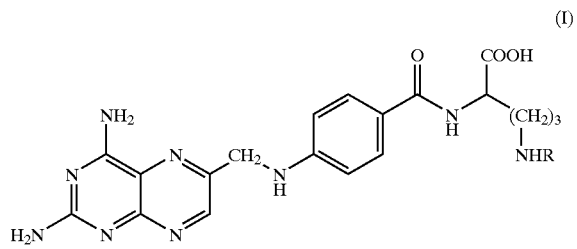

(I)

in which R is hydrogen. It has been reported to be a potent inhibitor of dihydrofolate reductase (DHFR) and of folylpolyglutamate synthetase (FPGS), but to be relatively inactive as an inhibitor of cell growth in culture, and it has been suggested that amino-substituted prodrug derivatives of it would be of interest because of possible increased cellular uptake. Rosowsky et al., J. Med. Chem., Vol. 29, pp 655–660 (1986).

A series of acidic compounds according to formula I were disclosed in U.S. Pat. No. 4,767,761 in which R is a benzoate derivative, e.g., —CO—Ar—COOR$^1$ where Ar is an aromatic group and R$^1$ is hydrogen or lower alkyl having I to 5 carbon atoms. Such compounds are hereinafter referred to as acidic compounds of Formula Ia.

The acidic compounds of Formula Ia disclosed in '761 exhibit remarkably high inhibitory activity against the growth of tumor cells resistant to methotrexate, such as the human cell lines SCC 15/R1 and SCC 25/R1. The inhibitory activity of acidic compounds of Formula Ia was unexpectedly higher than inhibitory activity for other $N^\delta$-acyl derivatives of APA-L-Orn. Acidic compounds according to Formula Ia are subject to gradual decomposition when stored in a dry state as a powder or when stored in an alkaline solution having a pH of greater than about 7.5, or more typically a pH of between about 7.5 and 9. Further, acidic compounds according to Formula Ia are not soluble in aqueous solutions without the addition of a basic additive.

It would be desirable to have new formulations of compounds according to Formula Ia which have good shelf-life in dry formulations and are readily soluble in water without the addition of basic additives. Particularly desirable would be pharmaceutically acceptable salts of compounds of Formula Ia which exhibit high inhibitory activity against the growth of methotrexate-resistant cells and which have increased stability as compared to the corresponding acidic compound of Formula Ia.

SUMMARY OF THE INVENTION

We have now discovered a new class of ammonium salts of $N^\delta$-acylated $N^\alpha$-(4-amino-4-deoxypteroyl)-4-ornithine compounds and therapeutic compositions comprising same. The present invention also features methods of treating patients suffering from or susceptible to cancer, particularly patients suffering from or susceptible to cellular tumor growth, tumor proliferation or metastasis by administering an ammonium salt of the invention exhibiting high inhibitory activity against the growth of methotrexate-resistant cells to a patient suffering from cancer. The ammonium salts of the invention possesses a superior combination of aqueous solubility and improved chemical stability as compared to the corresponding acidic compounds of Formula Ia.

Ammonium salts of the invention exhibit superior chemical stability such that the ammonium salts of the invention have increased shelf-life as compared to the corresponding acidic compounds of Formula Ia. Improved chemical stability facilitates isolation of the ammonium salts of Formula II, facilitates formulation of pharmaceutical compositions comprising an ammonium salt of Formula II and increases the shelf life of both pure ammonium salt of Formula II and pharmaceutical compositions comprising an ammonium salt of Formula II.

The present invention features ammonium salts according to formula II:

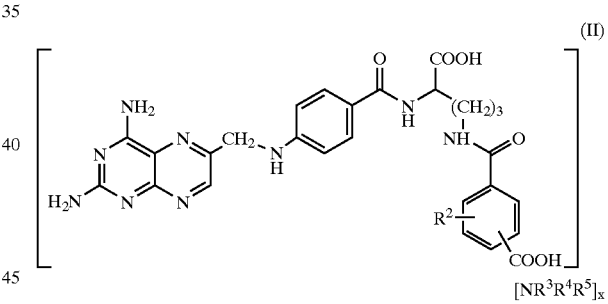

(II)

wherein:

R$^2$ represents up to four groups independently selected at each occurrence of R$^2$ from the group consisting of hydrogen, $C_{1-6}$ alkyl, $C_{2-6}$ alkenyl, $C_{2-6}$ alkynyl, $C_{3-8}$ cycloalkyl, $C_{1-6}$ alkoxy, chloro, fluoro, hydroxy, and —COOH;

R$^3$, R$^4$, and R$^5$ are independently selected from hydrogen and $C_{1-6}$ alkyl; or NR$^3$R$^4$ taken in combination form a 5 to 7 member heterocycle having at least one nitrogen ring atom; and x is a real number greater than 0 and less than about 4.

Preferred ammonium salts according to Formula II include those salts in which NR$^3$R$^4$R$^5$ represents ammonia, i.e., NH$^3$, piperazinium, 2-hydroxyethylammonium or a pharmaceutically acceptable alkaloid. More preferred are ammonium salts according to Formula II in which NR$^3$R$^4$R$^5$ represents ammonia.

Preferred compounds of Formula II are highly active inhibitors of growth in tumor cells resistant to methotrexate, particularly leukemia cells, lymphoblasts, human tumor cell lines SCC 15/R1 and SCC 25/R1, and the like.

The invention also provides pharmaceutical compositions comprising an ammonium salt of the above Formula II together with a pharmaceutically acceptable carrier.

Other aspects of the invention are discussed infra.

DETAILED DESCRIPTION OF THE INVENTION

In preferred embodiments, the present invention features ammonium according to Formula III:

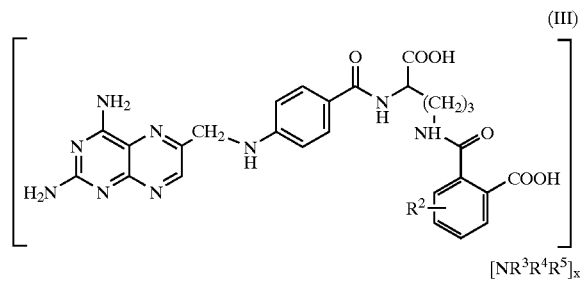

wherein x, $R^2$, $R^3$, $R^4$, and $R^5$ are as defined for salts of Formula II.

Preferred ammonium salts according to Formula III include those salts in which $NR^3R^4R^5$ represents ammonia, i.e., $NH^3$, piperazinium, 2-hydroxyethylammonium or a pharmaceutically acceptable alkaloid. More preferred are ammonium salts according to Formula III in which $NR^3R^4R^5$ represents ammonia.

The invention features preferred ammonium salts according to either Formula II or Formula III wherein $NR^3R^4R^5$ represents ammonia and x is less than about 4, 3.5, 3, or 2.5 and x is greater than about 0, 0.5, or 1. In preferred embodiments, x is a real number between about 0.75 and about 2.5, more preferably between about 0.8 and about 2.4 or between about 0.9 and about 2. More preferably, x is about 1, 1.1, 1.2, 1.3, 1.4, 1.5, 1.6, 1.7, 1.8, 1.9, or 2.0.

In a preferred embodiment, the invention provides ammonium salts according to Formula IV:

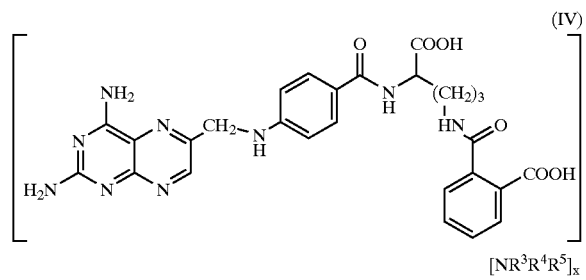

wherein $R^3$, $R^4$, and $R^5$ are independently selected from hydrogen and $C_{1-6}$ alkyl; or $NR^3R^4$ taken in combination form a 5 to 7 member heterocycle having at least one nitrogen ring atom; and x is a real number greater than 0 and less than about 4.

Preferred ammonium salts according to Formula IV include those salts in which $NR^3R^4R^5$ represents ammonia, i.e., $NH_3$, or a pharmaceutically acceptable alkaloid. More preferred are ammonium salts according to Formula IV in which $NR^3R^4R^5$ represents ammonia.

In a preferred embodiment, the invention provides an ammonium salt of Formula IV, wherein $NR^3R^4R^5$ represents ammonia, the ammonium salt comprises 1 to 2 equivalents of ammonia, e.g., $1 \leq x \leq 2$ and the ammonium salt optionally further comprises hydrating water.

Methods of Making Ammonium Salts of the Invention:

All suitable methods of forming an ammonium salt from a corresponding carboxylic acid or metal carboxylate are contemplated for use in preparing ammonium salts provided by the present invention. Preferred methods for preparing ammonium salts according to any one of Formula II, III, or IV, where $NR^3R^4R^5$ is $NH_3$, include solvating the corresponding free acid in dilute aqueous ammonium hydroxide, removing any insoluble material by filtration, and lyophilizing the aqueous solution to afford pure ammonium salt.

In another embodiment, the invention provides methods for preparing ammonium salts according to any one of Formula II, III, or IV, comprising solvating the free acid in an appropriate solvent and introducing an amine of the formula $NR^3R^4R^5$ as a gas or a liquid into the solution of the free acid composition such that an ammonium salt according to Formula II, III, or IV precipitates from solution. Typically, where the amine is a gas, such as ammonia or methyl amine, a gaseous mixture comprising at least the gaseous amine is bubbled into the solution. Where the amine is a liquid, pure amine or a solution of amine in a water miscible liquid is introduced into the solution of free acid to induce ammonium salt formation.

Compounds suitable for use in the methods of the present invention include any and all different single pure isomers and mixtures of two or more isomers. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with a enantiomerically enriched compound, a racemate, or a mixture of diastereomers. Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral pyrrolidone compound is administered.

As also discussed above, typical subjects for administration in accordance with the invention are mammals, such as primates, especially humans.

Other preferred ammonium salts of the invention according to Formula II to IV include those ammonium salts capable of inhibiting growth of methotrexate-resistant cells with an $IC_{50}$ of 1 $\mu$M or less where methotrexate-resistant cells include carcinoma cells such as murine leukemia cells or human lymphoblasts. More preferably, ammonium salts of the invention have a cell growth inhibition $IC_{50}$ of 500 nM, 250 nM, 100 nM, 50 nM, 25 nM, or less against carcinoma cells. Most preferred compounds have a cell growth inhibition $IC_{50}$ of 25 nM, 20 nM, 15 nM, 10 nM, 5 nM, 2 nM, 1 nM or less against carcinoma cells, sarcoma cells or other neoplastic cells Other preferred ammonium salts of the invention exhibit cell growth inhibition which is about the same as the cell growth inhibition exhibited by the corresponding acidic $N^\delta$-acyl derivatives of $N^\alpha$-(4-amino-4-deoxypteroyl)-L-ornithine compounds disclosed in U.S. Pat. No. 4,767,761.

The present invention also features pharmaceutical compositions comprising an ammonium salt according to any one of Formula II–IV and a pharmaceutically acceptable carrier.

A pharmaceutical composition of the invention also may be packaged together with instructions (i.e. written, such as a written sheet) for treatment of a cancer as disclosed herein, e.g. instruction for treatment of a subject that is susceptible to or suffering from cancer, even more preferably a subject that is susceptible to or suffering from carcinomas exhibiting tumor cell growth which cells are resistant to methotrexate.

Preferred methods of the invention include methods of identifying and/or selecting a subject (e.g. mammal, particularly human) that is suffering from a cancer or growth of tumor cells resistant to methotrexate, such as carcinomas, sarcomas, and other neoplastic cells, as disclosed herein.

Suitable halogen substituent groups or halide groups of compounds of the invention, including compounds of Formula I, II, III, IV, and V as defined above, include F, Cl, Br and I. Alkyl groups of compounds of the invention preferably have from 1 to about 12 carbon atoms, more preferably 1 to about 8 carbon atoms, still more preferably 1 to about 6 carbon atoms. As used herein, the term alkyl unless otherwise modified refers to both cyclic and noncyclic groups, although of course cyclic groups will comprise at least three carbon ring members. Straight or branched chain noncyclic alkyl groups are generally more preferred than cyclic groups, particularly branched chain groups such as isopropyl and t-butyl. Preferred alkenyl groups of compounds of the invention have one or more unsaturated linkages and from 2 to about 12 carbon atoms, more preferably 2 to about 8 carbon atoms, still more preferably 2 to about 6 carbon atoms. The term alkenyl as used herein refer to both cyclic and noncyclic groups, although straight or branched noncyclic groups are generally more preferred, particularly branched chain groups. Preferred alkoxy groups of compounds of the invention include groups having one or more oxygen linkages and from 1 to about 12 carbon atoms, more preferably from 1 to about 8 carbon atoms, and still more preferably 1 to about 6 carbon atoms. Preferred thioalkyl groups of compounds of the invention include those groups having one or more thioether linkages and from 1 to about 12 carbon atoms, more preferably from 1 to about 8 carbon atoms, and still more preferably 1 to about 6 carbon atoms. Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms. Preferred arylamino groups include those groups having an amino group substituted with one or two aryl groups. Preferred heteroarylamino groups include those groups having an amino group substituted with one or two heteroaryl groups. Substituted and unsubstituted mono and dialkylamino groups are particularly preferred, especially where each alkyl chain of the group has from 1 to about 6 carbon atoms. Preferred alkylsulfoxide of compounds of the invention have one or more sulfoxide groups, more typically one sulfoxide group, and from 1 to about 12 carbon atoms, more preferably 1 to about 8 carbon atoms, still more preferably 1 to about 6 carbon atoms. Preferred sulfonoalkyl groups of compounds of the invention have one or more sulfono ($SO_2$) groups, more typically one or two sulfono groups, and from 1 to about 12 carbon atoms, more preferably 1 to about 8 carbon atoms, still more preferably 1 to about 6 carbon atoms. Preferred alkanoyl groups of compounds of the invention include groups having one or more carbonyl groups, more typically one or two carbonyl groups, and from 1 to about 12 carbon atoms, more preferably 1 to about 8 carbon atoms, still more preferably 1 to about 6 carbon atoms. Preferred alkoxycarbonylamino groups include those groups of the formula —NHCOOR where R is substituted or unsubstituted alkyl having from 1 to about 10 carbon atoms, more preferably 1 to about 6 carbon atoms. Suitable heteroaromatic groups of compounds of the invention contain one or more N, O or S atoms and include, e.g., quinolinyl, pyridyl, pyrazinyl, indolyl, carbazoyl, furyl, pyrrolyl, thienyl, thiazolyl, aminothiazolyl such as 2-aminothiazolyl, pyrazolyl, oxazolyl, imidazolyl, indolyl, benzofuranyl, benzothiazolyl and pyridyl including 2-pyridyls and 4-pyridyls, particularly pyridyl substituted at one or more ring positions by moieties such as hydroxy, alkanoyl such as acetate, alkylaminocarbonyl having from 1 to about 8 carbon atoms and alkoxycarbonyl having from 1 to about 8 carbon atoms. Suitable heteroalicyclic groups of compounds contain one or more N, O or S atoms and include, e.g., aziridinyl, azetidinyl, tetrahydrofuranyl, tetrahydropyranyl, pyrrolidinyl, 1,2,3,6-tetrahydropyridinyl, piperazinyl, piperidinyl, morpholinyl and thiomorpholinyl.

Substituted moieties of compounds of the invention, including substituted $R^2$, $R^3$, $R^4$, and $R^5$ groups, may be "optionally substituted," that is groups may be substituted at one or more available positions by one or more suitable groups such as, e.g., halogen such as fluoro, chloro, bromo and iodo; cyano; hydroxyl; nitro; alkyl groups including those groups having 1 to about 12 carbon atoms or from 1 to about 6 carbon atoms, preferably noncyclic alkyl groups including branched chain groups such as isopropyl and t-butyl; alkenyl and alkynyl groups including groups having one or more unsaturated linkages and from 2 to about 12 carbon or from 2 to about 6 carbon atoms; alkylthio groups including those moieties having one or more thioether linkages and from 1 to about 12 carbon atoms or from 1 to about 6 carbon atoms; and, in at least preferred aspects of the invention, alkoxy groups having one or more oxygen linkages and from 1 to about 12 carbon atoms or 1 to about 6 carbon atoms; and aminoalkyl groups such as groups having one or more N atoms (which can be present as primary, secondary and/or tertiary N groups) and from 1 to about 12 carbon atoms or from 1 to about 6 carbon atoms.

The ammonium salts of the invention may be administered topically, parenterally, by inhalation or spray or rectally in dosage unit formulations containing conventional non-toxic pharmaceutically acceptable carriers, adjuvants and vehicles. Parenteral administration of an aqueous solution of one of the ammonium salts of the invention is particularly preferred. The term parenteral as used herein includes injections and the like, such as subcutaneous, intradermal, intravascular (e.g., intravenous or intraarterial), intramuscular, intrasternal, spinal, intrathecal, and like injection or infusion techniques, with subcutaneous, intramuscular and intravascular injections or infusions being preferred.

In addition, there is provided a pharmaceutical formulation comprising a compound of the invention and a pharmaceutically acceptable carrier. One or more compounds of the invention may be present in association with one or more non-toxic pharmaceutically acceptable carriers and/or diluents and/or adjuvants and if desired other active ingredients. Typical pharmaceutical compositions comprise an ammonium salt of the invention mixed with a conventional excipient, i.e., pharmaceutically acceptable organic or inorganic carrier substances suitable for a desired route of administration which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, L-arginine, mannitol polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Compounds of the invention may be administered parenterally, preferably in a sterile non-toxic, pyrogen-free medium. The drug, depending on the vehicle and concentration used, can either be suspended or dissolved in the vehicle. Advantageously, adjuvants such as local anesthetics, preservatives and buffering agents can be dissolved in the vehicle. The pharmaceutical compositions containing compounds of the invention may be in a form suitable for parenteral use, for example, as aqueous solutions, or dry powder compositions such as the solid residue produced by lyophilizing an aqueous solution of the ammonium salt of the invention. Typically for parenteral use, sterile water or a sterile pharmaceutically acceptable aqueous solution is added to a vacuum vial comprising a dry powder composition of an ammonium salt of the invention prior to administration.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example coloring agents, may also be present.

Synthetic Methodology $N^\alpha$-(4-Amino-4-deoxypteroyl)-$N^\delta$-hemiphthaloyl-L-ornithine (PT 523), compound 8, was prepared following the procedure as outlined in Scheme 1.

Condensation of 2,4,5,6-tetraaminopyrimidine with dihydroxyacetone gave 6-hydroxymethylpteridine 1. Compound 1 was treated with bromine and triphenyl phosphine in dimethylacetamide to give the corresponding 6-bromomethylpteridine which was coupled in situ with 4-aminobenzoic acid to afford pteroylbenzoic acid 2. Purity of the crude product was about 85% as analyzed by HPLC. Due to the low solubility of this compound in most solvents, purification by recrystallization proved to be impractical. The corresponding sodium salt, however, was soluble in hot water and crystallized upon cooling. Although compound 2 decomposes in hot aqueous hydroxide, treatment of the crude product with dilute sodium bicarbonate gave the sodium salt without observable decomposition. Recrystallization of the salt from dilute aqueous bicarbonate raised product purity to 93% or above. The purified salt was then converted back to acid 2 by treatment with aqueous acetic acid.

Formylation of compound 2 proceeded readily and gave good quality intermediate 3. This material was coupled with ornithinate 5 to give compound 6, which had better solubility characteristics and was purified by column chromatography. Base hydrolysis of compound 6 under the reaction conditions used for the nonformyl analog (methanol-THF as solvent) did not give good quality product 7. Opening of the phthalimide and hydrolysis of the methyl ester proceeded readily but cleavage of the formyl group was slow and incomplete. Better results were obtained by replacing THF with dimethyl sulfoxide as a cosolvent. Thus, with six equivalents of base in DMSO-methanol (1:4), the reaction went to completion in 30–45 min. At shorter reaction periods, the product contained some unreacted N-formyl compound and by extending the reaction time, formation of several other impurities was observed. For this reason, the hydrolysis step was carried out in multiple, small scale runs (2–10 g) and reaction progress was closely monitored (HPLC).

In our first attempt to obtain a uniform 10–15 g lot of compound 7, several small batches of 93–96% pure product were combined, dissolved in dilute aqueous bicarbonate, and the compound was reprecipitated by the addition of acid. This proved to be an unacceptable procedure. A major impurity was generated and the uniform lot now had a purity of only 85%. Our attempts to repurify the compound, failed. As an alternative approach, we established that compound 7 was relatively stable when dissolved in dilute ammonium hydroxide. Lyophilization of the solution gave the ainmonium salt 8 in the form of a yellow powder. Product decomposition, if any, was minimal.

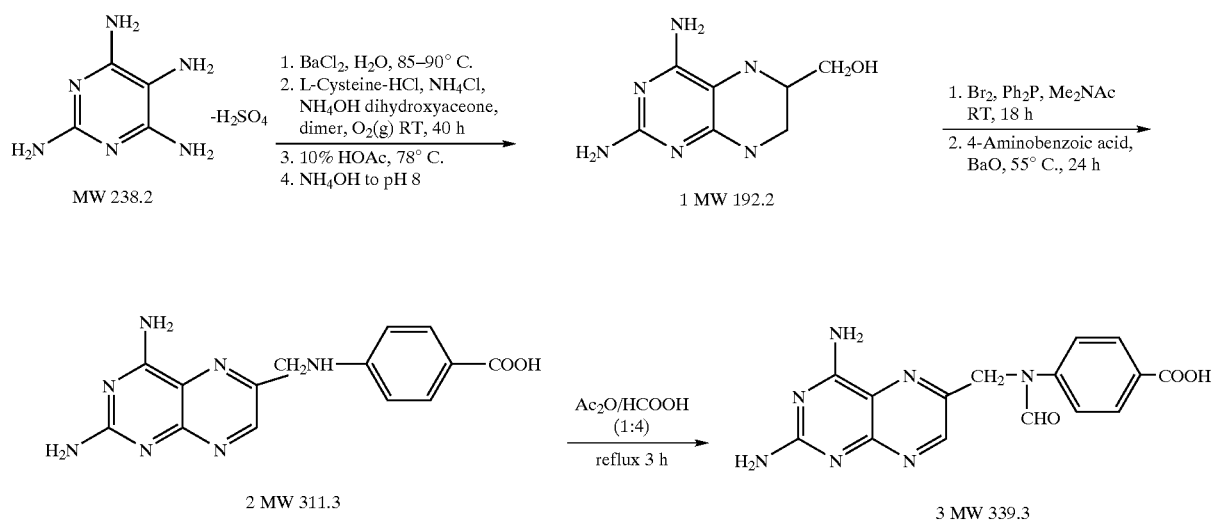

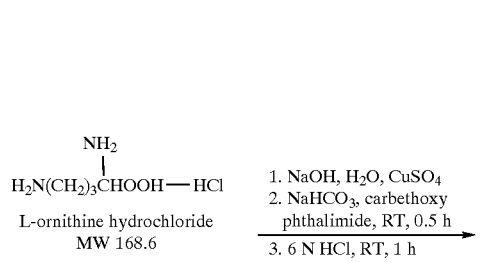
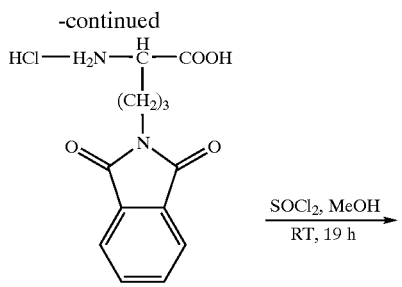
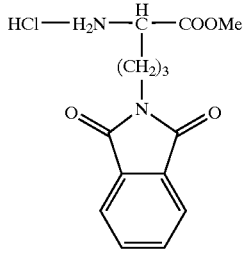
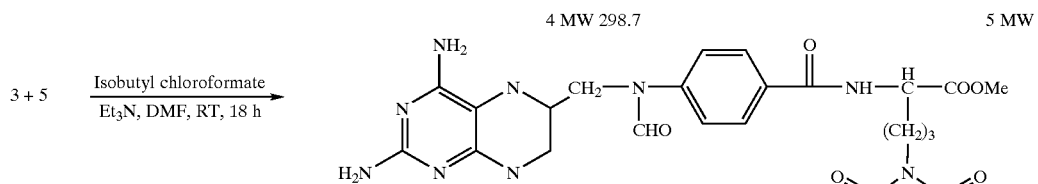
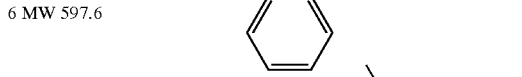
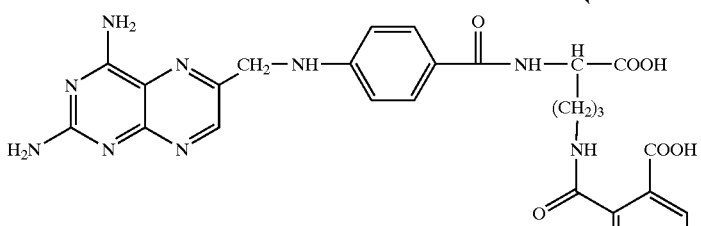
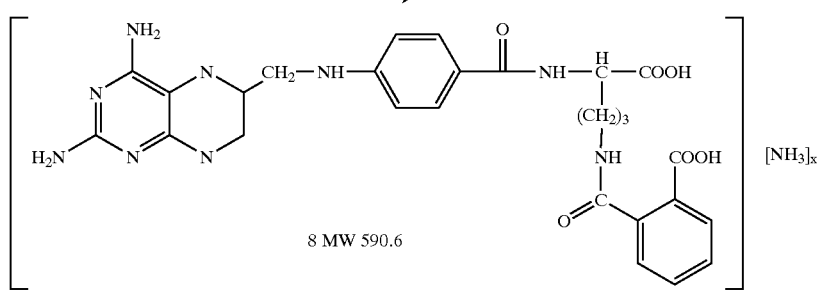

The title compound was prepared, following literature procedures, via the sequences shown above. The condensation of 2,4,5,6-tetraaminopyrimidine with dihydroxyacetone generated 6-hydroxymethyl pteridine (1). This was converted to the corresponding bromide and coupled in situ with 4-aminobenzoic acid to give pteroic acid 2. Compound 2 was formylated in a mixture of refluxing formic acid and acetic anhydride to afford formylpteroic acid 3 (24% overall).

The other part of the molecule was prepared from L-ornithine hydrochloride. Thus, L-ornithine hydrochloride was converted to the corresponding copper complex, coupled with carbethoxyphthalimide in the presence of sodium bicarbonate, then treated with hydrochloric acid to form hydrochloride 4. Esterification of 4 with methanol in the presence of thionyl chloride gave methyl ornithinate 5 (43% overall).

The condensation of formylpteroic acid 3 with methyl ornithinate 5 was effected using the mixed anhydride method (isobutylchloroformate and triethylamine) to give compound 6 (63% from 3). The conversion of intermediate 6 to "PT523" 7 was achieved by careful hydrolysis with 2N sodium hydroxide in a mixture of methanol and dimethyl sulfoxide (4:1) at room temperature for 30 min (90%). Finally, different batches of 7 were combined into two 50–55 g lots and each was converted into ammonium salt 8 by dissolving in dilute ammonium hydroxide, followed by lyophilization. Samples of 55 g and 54 g of "PT523" (as $NH_4^+$ salt, HPLC purity 96.5%+) were shipped to the NCI on Jan. 26, 2000 as Lot Nos. ML-07G-15, and ML-07G-23.

EXAMPLES

Example 1

4-Amino-4-deoxy-6-hydroxymethylpteridine (1)

Tetraaminopyrimidine sulfate (119 g, 0.5 mol) was added to a solution of barium chloride (122 g, 0.5 mol) in water (2.5 L) at 80° C. The suspension was stirred at 85–90"C for 15 min, then cooled to 35° C. and filtered. The combined filtrate was placed in a three-necked 5 L flask equipped with efficient mechanical stirrer and a fritted-glass tube for oxygen inlet. L-Cysteine hydrochloride (87.8 g, 0.5 mol) was added, followed by ammonium chloride (642 g, 12 mol) and ammonium hydroxide (63 mL, 1 mol, diluted with 1 L of water). The mixture was cooled under oxygen to 0° C. (acetone/$CO_2$ bath) and dihydroxyacetone dimer (135 g, 0.75 mol) was added. The pH of the reaction mixture was adjusted to 6 (with approx. 4 mL conc. $NH_4OH$), the cooling bath was removed, and the mixture was stirred vigorously under oxygen flow for 40 h. The solid 1 (predominantly the hydrochloride salt) was collected by filtration, washed with water (2×100 mL) and ethanol (100 mL), and dried under reduced pressure at 100° C. overnight.

The dried hydrochloride salt (114.0 g, 0.5 mol) was added to hot (75° C.) water (2052 mL) containing glacial acetic acid (205 mL, 3.4 mol). The suspension was stirred at 75–80° C. for 15 min. The insoluble material was removed by filtration and the clear filtrate was treated with Norit type charcoal at 85° C. for 5 min. After filtration, the mixture was cooled to 45° C., and adjusted to pH 6 with conc. $NH_4OH$ (245 mL, 19 mol). The bright yellow precipitate was collected, washed with water (100 mL), ethanol (100 mL) and finally with a small amount of ether. The product was dried under reduced pressure at 100° C. overnight to give 66.0 g (68%) of bright yellow solid, Lot JK-1-106.

The above described procedure was repeated two more times to produce 54.0 g (56%), Lot JK-1-108, and 60.0 g (64%), Lot JK 1-112.

The combined lots JK-1-106, JK-1-108, and JK-1-112 (179 g, 0.92 mol) were dissolved in 10% aq. acetic acid (3.6 L, 5.99 mol) at 75° C., with the aid of conc. HCl (65 mL, 0.8 mol). The orange solution was treated with Norit charcoal (30 g), filtered and cooled to 40° C. The solution was neutralized with conc. $NH_4OH$ (435 ml, 6.9 mol). The bright yellow solid was collected, washed with water (2×200 mL), ethanol (200 mL), and ether (100 mL). The product was dried under reduced pressure at 100° C. overnight, to give 163.2 g (57% from tetraaminopyrimidine sulfate) of bright yellow solid, Lot JK-1-114; HPLC purity: 96.0% (Column—prontosil 120-3-C18 AQ, 4.6×150 mm, 3.0$\mu$; detector at 254 nm; Mobile phase—2 to 20% acetonitrile in 0.01% aqueous TFA from 2 min to 7 min, 1 mL/min; Sample—0.5 mg/mL, 10 $\mu$L injection).

Example 2

4-Amino-4-deoxypteroic Acid (2)

To a 2 L 3-necked round bottom flask, equipped with a dropping funnel, a thermometer, and a drying tube, were added triphenylphosphine (216 g, 0.83 mol) and anhydrous dimethylacetamide (0.66 L). The resulting clear solution was cooled to 5° C. and bromine (132 g, 0.83 mol) was added over 45 min while maintaining the temperature below 8° C. To the resulting white slurry was added 2,4-diamino-6-hydroxymethyl pteridine (53 g, 0.28 mol). The temperature rose to 35° C. due to exothermic effect. The rust colored slurry slowly dissolved over 1 h to become a dark red solution. The mixture was stirred at ambient temperature overnight (ca. 17 h) forming a dark red slurry. Barium oxide (53 g, 0.35 mol) and 4-aminobenzoic acid (57 g, 0.42 mol) were added in one portion each with vigorous stirring. The temperature rose to 70° C. due to exothermic effect and the mixture turned to a rust-colored slurry within 15 min. The reaction mixture was stirred at 55±2° C. for 24±2 h. The resulting yellow-brown slurry was cooled to 20° C., then poured into a mixture of $CH_2Cl_2$ (6.9 L) and MeOH (0.2 L). The solids were isolated by filtration, slurried in $H_2O$ (2.5 L), and the mixture was filtered again to isolate the solids. The solids were slurried in MeOH (2.5 L), isolated by filtration, and air-dried at ambient temperature, to give 85 g (99%) of crude product as a brownish-yellow powder, Lot BM-02G-54.

In a similar manner additional 1 (106 g) was processed in two lots, to give 83 g (Lot BM-02G-56) and 85 g (Lot BM-02G-57) of crude 2.

The combined crude 2 (Lot BM-02G-54, -56, -57; 250 g) was slurried in methanol (10 L). The mixture was heated at reflux for 30 min with vigorous stirring. The mixture was cooled to 25° C., filtered, and the solids were air-dried at ambient temperature overnight (ca. 16 h) to give 238 g of brownish yellow powder (95% recovery), Lot BM02G-58.

Example 3

Conversion to $Na^+$ Salt

Step A: The above solid (237 g, Lot BM-02G-58) was stirred in 4% aqueous $NaHCO_3$ (9–5 L) at 85° C. for 15–20 min. The undissolved material was isolated by filtration and air-dried for 16 h yielding 91 g of brown solid (Lot BM-02G-59A). The filtrate was treated with Norit charcoal (35 g), filtered hot (85° C.) and allowed to cool to 20–25° C. overnight. A yellow precipitate was isolated by filtration and air-dried at ambient temperature overnight (ca. 18 h) to give 109 g of a brownish yellow solid, Lot BM-02G-59B.

Step B: The undissolved brown solid from above (91 g, Lot BM-02G-59A) was slowly heated in 4% aqueous $NaHCO_3$ (7.1 L) to 90° C. Norit charcoal (10 g) was added to the solution and the mixture was stirred for 15 min at 90° C. The charcoal was removed by filtration and the filtrate was allowed to cool to 20–25° C. overnight. (Precipitation of a yellow solid occurred 15 min after the charcoal filtration at ~65° C.). The slurry was filtered and the isolated solid was air-dried to give 72 g of 2 as the sodium salt, Lot No. BM-02G-61.

Example 3a

Alternate Process of Conversion to the $Na^+$ Salt

Step A and Step B of Example 3 may be combined into a single step, where solid 2 obtained in Example 2 is stirred in 4% aqueous $NaHCO_3$ at 90° C. for 15–20 min. Trace undissolved material is isolated by hot filtration. The filtrate is then treated with Norit charcoal (35 g), filtered hot (~65" C) and allowed to cool to 20–25° C. overnight. A yellow precipitate of the sodium salt of 2 is then isolated by filtration and air-dried at ambient temperature.

Example 4

Recrystallization of $Na^+$ Salt

The brownish yellow material (107 g, Lot BM-02G-59B) was dissolved in 1% aqueous sodium bicarbonate (4.1 L) at 90° C. The solution was treated with Norit activated charcoal, stirred for 15 min at 90° C., and filtered. The product began to precipitate immediately following the filtration. The slurry was allowed to cool to 25° C., then cooled further on ice to 15° C. The solid was isolated by filtration and air-dried overnight to give 95 g of a bright yellow solid, Lot BM-02G-62.

Example 5

Conversion of $Na^+$ Salt to Free Acid (2)

The combined sodium salt (71 g, Lot BM-02G-61, and 94 g, Lot BM-02G-62) was dissolved in water (18 L) containing sodium bicarbonate (30 g) at 85° C. The resulting orange solution was filtered hot to remove small amount of insoluble material (9.5 g after drying) which was discarded. The hot filtrate was acidified with acetic acid (0.1 L) to pH 4. The resulting slurry was cooled to 25° C. in an ice-water bath. The solid was collected by filtration, rinsed with cold water (0.5 L, 10° C.), air-dried overnight, then dried at 70±5° C./30 in Hg for 5 h to give 117 g (46%) of compound 2 as a yellow-orange solid, Lot BM-02G-63B; HPLC purity: 96.9% (Column—prontosil 120-3-C 18 AQ, 4.6×150 mm, 3.0μ, detector at 254 nm; Mobile Phase—20% methanol in aqueous 10 nM Tris, pH 8.0 (with dilute HCl), 1 mL/min; Sample—0.05 mg/mL, 10 μL injection).

Example 6

4-Amino-4-deoxy-$N^{10}$-formylpteroic Acid (3)

Acetic anhydride (510 mL, 5.4 mol) was added in one portion to concentrated (96%) formic acid (2.05 L, 54.3 mol). After the exothermic effect subsided (45 min), the pteroic acid 2 (54 g, 0.17 mol) was introduced at 38° C. The reaction mixture was then heated at reflux for 3 h. The mixture was concentrated to dryness under reduced pressure (~40 mm Hg). The beige solid was taken into water (3.8 L) containing conc. ammonium hydroxide (0.54 L, 8.4 mol). The suspension was heated to dissolution (70° C.), a small amount of insoluble material was removed by filtration, and the filtrate was labeled Lot BM-02G-72.

Additional pteroic acid 2 (62 g, 0.20 mol) was formylated in the same manner as described above, yielding a filtrate labeled Lot BM-02G-73.

The two filtrates (BM-02G-72 & 73) were combined and cooled to 35° C. The mixture was acidified with acetic acid (0.95 L) to pH 5.5 (pH paper). The resulting slurry was cooled further to 20° C. The solid was isolated by filtration and air-dried overnight. This material was resuspended in water (7.0 L) containing acetic acid (0.26 L) at 40±5° C. The suspension was stirred vigorously for 0.5 h, filtered, and the solid was washed successively with water (2×0.5 L), ethanol (0.5 L) and ether (0.1 L) to give 130 g (>100%) of 3 as an off-white solid after air drying for 24 h. The solid (130 g) was slurried in water (7.0 L) containing acetic acid (0.35 L) at 40±5"C for 4 h. The solid was isolated by filtration, rinsed with water (1.0 L) and air-dried for 36 h. The off-white solid was then dried further at 70±5° C./30 in Hg for 3 h to give 126 g (91%) of compound 3 as a 1.75 hydrate, Lot BM-02G-76. Anal. Calcd for $C_{15}H_{13}N_7O_3 \cdot 1.75H_2O$: C, 48.58; H, 4.48; N, 26.44. Found: C, 48.55; H, 4.38; N, 26.63.

Example 7

$N^\delta$-Phthaloyl-L-ornithine hydrochloride (4)

L-Ornithine hydrochloride (100 g, 0.59 mol) was dissolved in water (1.0 L) containing sodium hydroxide (47.4 g, 1.18 mol). Cupric sulfate pentahydrate (74.0 g, 0.30 mol) in water (1.0 L) was mixed with the above solution producing a deep blue color. Sodium bicarbonate (59.2 g, 0.71 mol) and carbethoxyphthalimide (148 g, 0.65 mol) were added and the resulting light blue suspension was stirred at room temperature for 0.5 h. The precipitate was collected by filtration and washed successively with water (0.3 L×2), ethanol (0.3 L×2), and ether (0.3 L×3), and air-dried overnight to give 165 g of a blue solid. This copper salt of phthaloyl ornithine was then stirred with 6N hydrochloric acid (825 mL) at room temperature for 1 h. The mixture was filtered using a fritted glass filter and the solid was washed with 6N hydrochloric acid (1.25 L) until the filtrate was nearly colorless (very light green). The crude hydrochloride salt was sucked dry on the filter and then air-dried for 64 h to afford crude 4 (123 g, 70%) as a light green solid, Lot BM-02G-65A. The filtrate was refrigerated over the weekend and deposited more solid. The solid was isolated by filtration and air-dried for 4 h to give additional 4.5 g (2.5%) of a light green solid, Lot BM-02G-65B.

The crude $N^\delta$-phthaloyl-L-ornithine hydrochloride (4) (122 g, Lot BM-02G-65A, and 4.5 g, BM-02G-65B) was dissolved in methanol (1.3 L) at ambient temperature. This light green solution was diluted with ethyl acetate (3.5 L) while stirring. A precipitate formed immediately. The slurry was stirred for 30 min. The solid was isolated by filtration, rinsed with ethyl acetate (0.3 L), and air-dried at room temperature overnight to give 72 g of product (41% from L-ornithine hydrochloride), Lot BM-02G-67, mp 217–219° C. (dec.).

The above procedure was repeated two more times starting with 68 g and 130 g of L-ornithine hydrochloride to give 56 g (46%), Lot BM-02G-69 and 117 g (51%), Lot BM-02G-84 of purified product 4, mp 217–219° C. (dec.). Thin-Layer Chromatography: Analtech Silica Gel GF: Eluent: Ethyl acetate-ethanol-water (7:2:1); $R_f$: 0.33; Comment: homogeneous.

Example 8

Methyl $N^\delta$-phthaloyl-L-ornithinate hydrochloride (5)

A stirred suspension of $N^\delta$-phthaloyl-L-ornithinate hydrochloride (4) (126 g, 0.42 mol) in methanol (2.7 L) was cooled to −20° C., and thionyl chloride (350 mL, 4.8 mol) was added dropwise over a period of 45 min while maintaining the temperature below 0° C. A white precipitate appeared during the addition. After the addition, the cooling bath was removed and the reaction mixture was stirred at room temperature overnight (ca. 18 h). The resulting light yellow clear solution was concentrated (aspirator) to dryness and any remaining methanol was removed by codistillation with toluene (650 mL). The residue was triturated with a mixture of methanol (65 mL), ethyl acetate (650 mL) and acetone (650 ruL). The solid was collected by filtration, washed with hexanes (250 mL×2), and air-dried overnight, then dried further at 55±5° C./30 in Hg for 6 h to give pure 5 (123 g, 94%) as a white powder, mp 195–197° C., Lot BM-02G-70. Anal. Calcd for $C_{14}H_{17}N_2ClO_4$: C, 53.77; H, 5.48; N, 8.96; Cl, 11.34. Found: C, 53.78; H, 5.44; N, 8.96; Cl, 11.37.

Another batch of $N^\delta$-phthaloyl-L-ornithinate hydrochloride (116 g) was esterified in a similar manner to give 116 g of pure compound 5 (93% as a hemihydrate), mp 195–197° C., Lot BM-02G-85. Anal. Calcd for $C_{14}H_{17}N_2ClO_4 \cdot 0.5 H_2O$: C, 52.26; H, 5.64; N, 8.71; Cl 11.02. Found: C, 52.38; H, 5.64; N, 8.66; Cl, 11.13. Thin-Layer Chromatography: Analtech Silica Gel GF: Eluent: Methanol-methylene chloride (1:9); $R_f$ 0.66; Comment: homogeneous.

Example 9

Methyl $N^\alpha$-(4-amino-4-deoxy-$N^{10}$-formylpteroyl-$N^\delta$-phthaloyl-L-ornothinate (6)

Isobutyl chloroformate (3.9 mL, 30 mmol) was added to a suspension of the hydrated pteroic acid 3 (11.0 g, 30 mmol) in dry DMF (0.4 L) containing triethylamine (33.4 mL, 0.24 mol). Most of the solids dissolved, and the mixture was stirred for 20 min. Methyl $N^\delta$-phthaloyl-L-ornithinate hydrochloride (5) (9.4 g, 30 mmol) was added, and the mixture was stirred for 20 mm. The next portion of isobutyl chloroformate (1.9 mL, 15 mmol) was added. After 10 min, additional methyl ornithinate 5 (4.7 g, 15 mmol) was introduced. This sequence was repeated two more times, adding isobutyl chloroformate (1.0 mL, 8 mmol) and compound 5 (2.4 g, 8 mmol) respectively at 10 min intervals. After the last addition., the mixture was stirred at room temperature overnight. The mixture was concentrated to a semi-solid, orange residue (~80 mL). The residue was stirred vigorously with water (0.6 L), resulting in a yellow-brown precipitate. The solid was isolated by filtration, then slurried in methanol (0.4 L). The solid was recollected by filtration, washed with methanol (0.1 L), and air-dried for 2 h to give 21 g of crude product 6. The crude product was dissolved in methylene chloride-methanol (95:5, 110 mL) and the solution was applied onto a silica gel column (440 g, 5.5×38 cm) packed in neat methylene chloride (2 L). The column was eluted with methylene chloride-methanol (95:5, 0.4 L), followed by methylene chloride-methanol (90:10, 3.2 L). The fractions containing pure product (0.25 L each) were combined and concentrated to dryness to give 12.5 g of a bright yellow solid. The crude product (11.5 g,) was dissolved in a mixture of DMF (58 mL) and methanol (58 mL) at reflux. Hot (70° C.) ethyl acetate (575 mL) was slowly added to the solution with moderate stirring. The clear yellow solution was allowed to cool to room temperature and was slowly stirred overnight. The next day, the mixture was cooled to 4±2° C. for 2 h and filtered, air-dried, then dried at 80±5° C./30 in Hg for 14 h to give 11.9 g (67%) of pale yellow crystalline compound 6, Lot BM-02G-80; HPLC: 96.5%. The NMR spectrum showed that the product contained ca. 0.2 mol % of the three crystallization solvents. This partially solvated product was suitable for the transformation.

A second batch of hydrated 3 (58 g, 0.156 mol) was treated with isobutyl chloroformate and compound 5 in a similar manner. After removal of DMF, the residue was stirred with water (2.5 L) and the solid was collected and air-dried to give 143 g of crude product 6. This material was chromatographed as described above to give 101 g of purified product, Lot BM-02G-81. The purified product was stirred with water (2 L) overnight. The solid was isolated by filtration, rinsed with water (0.5 L), air-dried for 40 h, to give 90 g of yellow solid, Lot BM-020-87.

A portion of this material (5.0 g) was dissolved in refluxing methylene chloride-methanol (93:7, 0.55 L). Silica gel (10 g) and charcoal (0.2 g) were added and the mixture was stirred for 15 min while cooling to room temperature. The mixture was filtered through a pad of celite (5 g) and the celite pad was rinsed with methylene chloride (50 mL). The combined filtrate was concentrated to dryness, and the residue (4.3 g) was dissolved in a mixture of DMF (25 mL) and MeOH (25 mL) at reflux (72" C). Hot ethyl acetate (70° C., 0.25 L) was slowly added and the stirred solution was allowed to cool to ambient temperature. The resulting slurry was stirred overnight, then cooled to 8" C and filtered. The solid was rinsed with ethyl acetate (25 mL) and air dried at room temperature to a constant weight, to give 3.8 g of pale yellow crystals, Lot BM-02G-89; HPLC: 98.8%.

The remainder of Lot BM-02G-87 (84 g) was purified is a similar manner to give 63 g of pale yellow crystals, Lot BM-02G-92; HPLC: 98.0%. The combined yield was 66.8 g (72%).

A final batch of compound 6 was prepared in a similar manner starting with 54 g (0.15 mol) of compound 3. After silica gel column chromatography, 69 g (Lot BM-02G-95A) of solid residue was obtained from pure fractions, and 25 g (Lot BM-02G-95B) of less pure solid was obtained from fractions containing trace impurities (based on TLC). To remove residual DMF, both products (BM-02G-95A and 95B) were stirred vigorously in water (2 L and 1 L, respectively) for 4 h. The solids were isolated by filtration, rinsed with water, and air dried for 64 h, then dried further at 40±5° C./30 in Hg for 5 h to give 66 g (Lot BM-020-102A) and 22 g (Lot BM-02G-102B) of yellow solids, respectively. Lot BM-02G-102B was purified further as follows. The solid was dissolved in methylene chloride-methanol (93:7, 2.4 L) at reflux (~35° C.). Silica gel (44 g) and charcoal (1 g) were added, and the mixture was stirred for 30 min while cooling to room temperature. The mixture was filtered through a bed of celite (40 g) prepared in methylene chloride (0.25 L), and the celite was rinsed with methylene chloride-methanol (93:7, 269 mL). The combined filtrate was concentrated to a solid residue weighing 19 g. This material was combined with Lot BM-02G-102A (66 g) and dissolved in a mixture of DMF (435 mL) and methanol (435 mL) at reflux. Hot ethyl acetate (65° C., 4.3 L) was added slowly with stirring and the solution was allowed to cool to room temperature. Precipitation began approximately 15 min after heating was discontinued resulting in a slurry. The slurry was stirred overnight, then cooled to 5±5° C. for 2 h. The solid was isolated by filtration, rinsed with ethyl acetate (0.25 L), and air dried overnight to give 69 g of a crystalline yellow solid, Lot BM-02G-103 (HPLC 96.6%). Since the purity was lower than considered desirable (based on probe hydrolysis runs), this lot was retreated with silica gel (138 g) and charcoal (2.8 g) in methylene chloride-methanol (93:7, 7.6 L) as described above. The resulting 67 g of solid was recrystallized from DMF-MeOH-EtOAc (0.3 L-0.3 L-3.5 L) as before, to give 50 g of Compound 6 (56%) as a light yellow crystalline solid, Lot BM-02G-105; HPLC: 98.9% (Column—Phenomonex Kromasil C8, 100 Å, 4.6×250 mm, 10$\mu$; UV detector at 254 nm; Mobile Phase—26% to 62% methanol in 0.01% aqueous TFA, pH 2.4 (with triethylamine) over 10 min; Sample—ca. 1 mg/mL., 10 $\mu$L injection). Thin-Layer Chromatography: EM Separations Technology, Silica Gel 60 $F_{254}$; Eluent: Methylene chloride-methanol (9:1); $R_f$ 0.34; Comment: trace impurity at $R_f$ 0.24.

Example 10

$N^\alpha$-phthaloyl-L-ornithine (7)

To a suspension of the ornithinate 6 (9.2 g, 15.4 mmol), in a mixture of methanol (36.8 mL) and dimethyl sulfoxide (9.2 mL) cooled to 10° C. (ice-water bath), was added a 2N sodium hydroxide solution (46 mL, 92.0 mmol) over 2 min while maintaining the reaction temperature below 20° C. After the addition, the cold bath was removed and the mixture was stirred at room temperature for 30 min. The resulting clear yellowish brown solution was diluted with water (180 mL) and cooled to 10° C. The pH was adjusted to ca 8.5 with 1N hydrochloric acid (48 mL), and the solution was extracted with ethyl acetate (180 mL×3). The aqueous phase was diluted with water (370 mL), then adjusted further to ca. pH 4.7 with 1N acetic acid (55 mL.

The resulting gelatinous mixture was seeded and stirred at room temperature for 30 min. The solid was collected by filtration, washed with water (40 mL×4), ethanol (40 mL×3), and ether (40 mL×3), and air-dried. The solid was dried further at 25° C./0.1 mm Hg overnight (ca. 16 hr) to give compound 7, 7.8 g (88%), Lot ML-07G-O1, as a yellow powder. Thin-Layer Chromatography: Analtech Silica Gel GF; Eluent: $CH_2Cl_2$—MeOH-conc. $NH_4OH$ (5:4:1); $R_F$ 0.68; Comment: some tailing.

In the same manner, additional 6 (116 g) was processed in thirteen lots to afford 100.6 g of 7.

| Lot. | Yield |
|---|---|
| ML-07G-06 | 3.0 g (87%) |
| ML-07G-07 | 8.8 g (92%) |
| MIL-07G-08 | 8.7 g (91%) |
| ML-07G-09 | 8.8 g (92%) |
| ML-07G-10: | 8.5 g (89%) |
| MIL-07G-12 | 8.8 g (92%) |
| ML-07G-13 | 2.4 g (89%) |
| ML-07G-17 | 8.6 g (90%) |
| ML-07G-18 | 8.7 g (91%) |
| ML-07G-19 | 8.5 g (89%) |

Example 11

$N^\alpha$-(4-Amino-4-deoxypteroyl)$N^\delta$-hemiphthaloyl-L-ornithine ammonium salt (8)

The combined free acid 7, ML-07G-07, -08, -09, -10, -11, -12, -13 (54.0 g, 94.1 mmol) was suspended in water (200 mL). To the suspension was added 5% ammonium hydroxide solution (75 mL, 107 mmol) until a reddish brown clear solution was observed (pH 9.0). The solution was filtered through a celite pad (5.0 g) and lyophilized for ca. 30 h to give target compound 8 as a yellow powder, 55.6 g, which was equilibrated in the air at room temperature until constant weight, 56.4 g, Lot ML-07G-15 (93%, as a 2.4 hydrate).

In the same manner, the combined free acid 7, ML-07G-01, -06, -17, -18, -19, -20, -21 (52.8 g, 92.1 mmol) was processed to obtain additional target compound 8, 55.4 g, Lot ML-07G-23 (93%, as a 2.6 hydrate).

Physical and Analytical Data $N^\alpha$(4-Amino-4 deoxypteroyl)-$N^\delta$-hemiphthaloyl-L-ornithine ammonium salt Lot No. ML-07G-15, 55 g Melting Point: Above 175° C. (dec)

Appearance: Yellow powder

Elemental Analysis: Calcd for $C_{27}H_{27}N_9O_6$ 1.5 $NH_3$.2.4 $H_2O$ (642.35)

|   | Calcd | Found |
|---|---|---|
| C | 50.49 | 50.53 |
| H | 5.70 | 5.63 |
| N | 22.90 | 22.91 |

Infrared Spectrum: Consistent with structure.

NMR Spectrum: Consistent with structure.

HPLC Purity: 97.3%

Thin-Layer Chromatography: Analtech Silica Gel GF

| Eluent | $R_f$ | Comment |
|---|---|---|
| Methylene chloride-methanol-concd ammonium hydroxide (5:4:1) | 0.68 | Homogeneous |
| Water-methanol-concd ammonium hydroxide (1:9:0.25) | 0.90 | Trace tailing |

Approximate Solubility at Room Temperature:

Water: >20 mg/mL

Ethanol: <1 mg/mL

Dimethyl formamide: <1 mg/mL

Dimethyl sulfoxide: >10 mg/mL

Physical and Analytical Data $N^\alpha$-(4-Amino-4-deoxypteroyl)-$N^\delta$-hemiphthaloyl-L-ornithine ammonium salt Lot No. ML-07G-23, 54 g Melting Point: Above 175° C. (dec)

Appearance: Yellow powder

Elemental Analysis: Calcd for $C_{27}H_{27}N_9O_6$ 1.5 $NH_3$.2.6 $H_2O$ (645.95)

|   | Calcd | Found |
|---|---|---|
| C | 50.20 | 50.14 |
| H | 5.73 | 5.78 |
| N | 22.77 | 22.70 |

Infrared Spectrum: Consistent with structure.

NMR Spectrum: Consistent with structure.

HPLC Purity: 96.5% (attached)

Thin-Layer Chromatography: Analtech Silica Gel GF

| Eluent | $R_f$ | Comment |
|---|---|---|
| Methylene chloride-methanol-concd Amonium hydroxide (5:4:1) | 0.68 | Homogeneous |
| Water-methanol-concd ammonium Hydroxide (1:9:0.25) | 0.90 | Trace tailing |

Approximate Solubility at Room Temperature:

Water: >20 mg/mL

Ethanol: <1 mg/mL

Dimethyl formamide: <1 mg/mL

Dimethyl sulfoxide: >10 mg/mL

All references disclosed herein are incorporated by reference.

What is claimed is:

1. An ammonium salt of the compound of formula II:

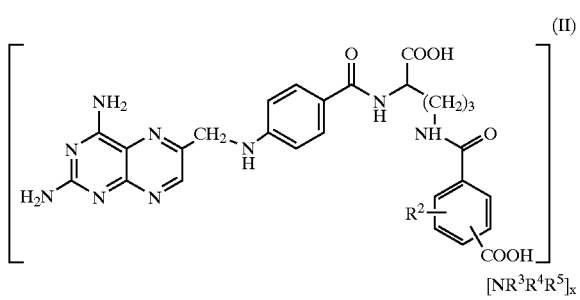

wherein:

$R^2$ represents up to four groups independently selected at each occurrence of $R^2$ from the group consisting of hydrogen, $C_{1-6}$ alkyl, $C_{2-6}$ alkenyl, $C_{2-6}$ alkynyl, $C_{3-8}$ cycloalkyl, $C_{1-6}$ alkoxy, chloro, fluoro, hydroxy, and —COOH;

$R^3$, $R^4$, and $R^5$ are each independently selected from hydrogen and $C_{1-6}$ alkyl; or $NR^3R^4$ taken in combination can form a 5 to 7 member heterocycle having at least one nitrogen ring atom; and x is a real number greater than 0 and less than about 4.

2. The compound of claim 1, wherein $NR^3R^4R^5$ represents ammonia, piperazinium, or 2-hydroxyethylammonium.

3. The compound of claim 2, wherein $NR^3R^4R^5$ represents ammonia.

4. An ammonium salt of the compound of formula III:

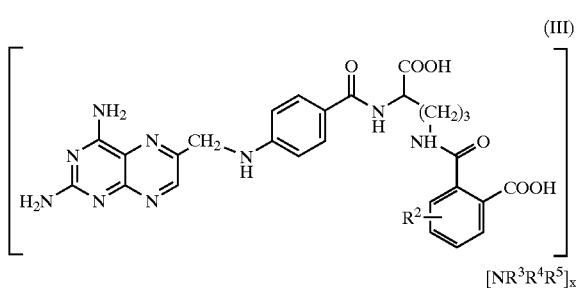

wherein:

$R^2$ represents up to four groups each independently selected at each occurrence of $R^2$ from the group consisting of hydrogen, $C_{1-6}$ alkyl, $C_{2-6}$ alkenyl, $C_{2-6}$ alkynyl, $C_{3-8}$ cycloalkyl, $C_{1-6}$ alkoxy, chloro, fluoro, hydroxy, and —COOH;

$R^3$, $R^4$, and $R^5$ are each independently selected from hydrogen and $C_{1-6}$ alkyl; or $NR^3R^4$ taken in combination form a 5 to 7 member heterocycle having at least one nitrogen ring atom; and x is a real number greater than 0 and less than about 4.

5. The compound of claim 4, wherein $NR^3R^4R^5$ represents ammonia, piperazinium, or 2-hydroxyethylammonium.

6. The compound of claim 5, wherein $NR^3R^4R^5$ represents ammonia.

7. The compound of claim 6, wherein x is a real number between about 0.5 and 3.

8. The compound of claim 7, wherein x is a real number between about 1 and about 2.

9. An ammonium salt of the compound of formula IV:

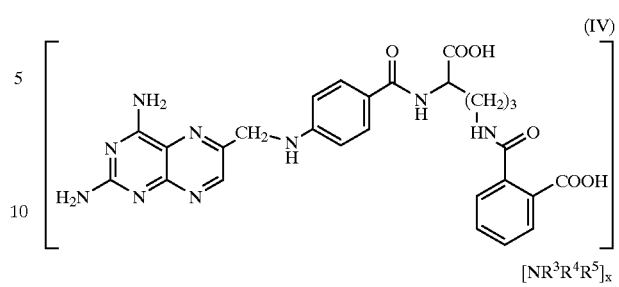

wherein:

$R^3$, $R^4$, and $R^5$ are each independently selected from hydrogen and $C_{1-6}$alkyl or $NR^3R^4$ taken in combination form a 5 to 7 member heterocycle having at least one nitrogen ring atom; and x is a real number greater than 0 and less than about 4.

10. The compound of claim 9, wherein $NR^3R^4R^5$ represents ammonia, piperazinium, or 2-hydroxyethylammonium.

11. The compound of claim 10, wherein $NR^3R^4R^5$ represents ammonia.

12. The compound of claim 11, wherein x is a real number between about 0.5 and 3.

13. The compound of claim 12, wherein x is a real number between about 1 and about 2.

14. The compound of claim 9, further comprising at least about 0.5 equivalents of water.

15. The compound of claim 14, wherein the water is present in an amount of from about 0.5 to about 5 equivalents.

16. An ammonium salt of the compound of formula V:

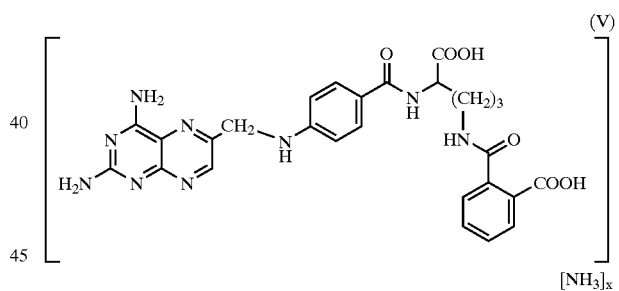

wherein x is a real number greater than 0 and less than about 4.

17. The compound of claim 16, wherein x is a real number between about 0.5 and 3.

18. The compound of claim 17, wherein x is a real number between about 1 and about 2.

19. The compound of claim 16, further comprising at least about 0.5 equivalents of water.

20. The compound of claim 19, wherein the water is present in an amount of from about 0.5 to about 5 equivalents.

21. The compound of claim 1, wherein the compound is capable of inhibiting the growth of methotrexate-resistant cells with an $IC_{50}$ of 1 µM or less.

22. The compound of claim 21, wherein the compound is capable of inhibiting the growth of methotrexate-resistant cells with an $IC_{50}$ of 500 nM or less.

23. The compound of claim 22, wherein the compound is capable of inhibiting the growth of methotrexate-resistant cells with an $IC_{50}$ of 100 nM or less.

24. The compound of claim 23, wherein the compound is capable of inhibiting the growth of methotrexate-resistant cells with an IC$_{50}$ of 10 nM or less.

25. The compound of claim 24, wherein the compound is capable of inhibiting the growth of methotrexate-resistant cells with an IC$_{50}$ of 1 nM or less.

26. The compound of claim 4, wherein the compound is capable of inhibiting the growth of methotrexate-resistant cells with an IC$_{50}$ of 1 $\mu$M or less.

27. The compound of claim 26, wherein the compound is capable of inhibiting the growth of methotrexate-resistant cells with an IC$_{50}$ of 500 nM or less.

28. The compound of claim 27, wherein the compound is capable of inhibiting the growth of methotrexate-resistant cells with an IC$_{50}$ of 100 nM or less.

29. The compound of claim 28, wherein the compound is capable of inhibiting the growth of methotrexate-resistant cells with an IC$_{50}$ of 10 nM or less.

30. The compound of claim 29, wherein the compound is capable of inhibiting the growth of methotrexate-resistant cells with an IC$_{50}$ of 1 nM or less.

31. The compound of claim 9, wherein the compound is capable of inhibiting the growth of methotrexate-resistant cells with an IC$_{50}$ of 1 $\mu$M or less.

32. The compound of claim 31, wherein the compound is capable of inhibiting the growth of methotrexate-resistant cells with an IC$_{50}$ of 500 nM or less.

33. The compound of claim 32, wherein the compound is capable of inhibiting the growth of methotrexate-resistant cells with an IC$_{50}$ of 100 nM or less.

34. The compound of claim 33, wherein the compound is capable of inhibiting the growth of methotrexate-resistant cells with an IC$_{50}$ of 10 nM or less.

35. The compound of claim 34, wherein the compound is capable of inhibiting the growth of methotrexate-resistant cells with an IC$_{50}$ of 1 nM or less.

36. The compound of claim 16, wherein the compound is capable of inhibiting the growth of methotrexate-resistant cells with an IC$_{50}$ of 1 $\mu$M or less.

37. The compound of claim 36, wherein the compound is capable of inhibiting the growth of methotrexate-resistant cells with an IC$_{50}$ of 500 nM or less.

38. The compound of claim 37, wherein the compound is capable of inhibiting the growth of methotrexate-resistant cells with an IC$_{50}$ of 100 nM or less.

39. The compound of claim 38, wherein the compound is capable of inhibiting the growth of methotrexate-resistant cells with an IC$_{50}$ of 10 nM or less.

40. The compound of claim 39, wherein the compound is capable of inhibiting the growth of methotrexate-resistant cells with an IC$_{50}$ of 1 nM or less.

41. A pharmaceutical composition comprising
(i) an ammonium salt of the compound of formula II:

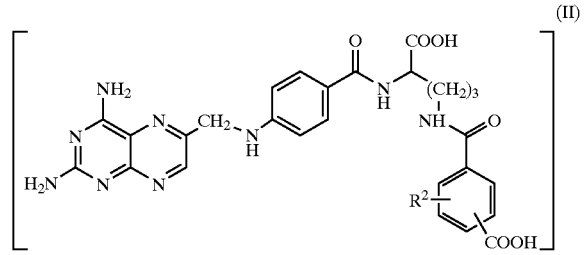

(II)

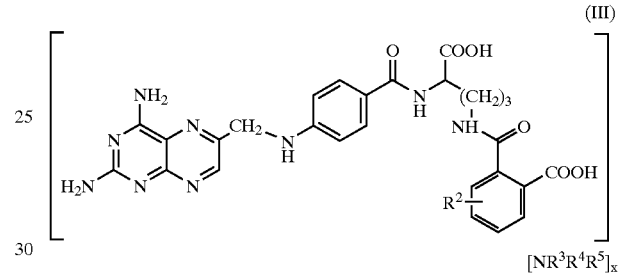

[NR$^3$R$^4$R$^5$]$_x$ wherein:
R$^2$ represents up to four groups independently selected at each occurrence of R$^2$ from the group consisting of hydrogen, C$_{1-6}$ alkyl, C$_{2-6}$ alkenyl, C$_{2-6}$ alkynyl, C$_{3-8}$ cycloalkyl, C$_{1-6}$ alkoxy, chloro, fluoro, hydroxy, and —COOH;

R$^3$, R$^4$, and R$^5$ are each independently selected from hydrogen and C$_{1-6}$ alkyl; or NR$^3$R$^4$ taken in combination can form a 5 to 7 member heterocycle having at least one nitrogen ring atom; and x is a real number greater than 0 and less than about 4; and
(ii) a pharmaceutically acceptable carrier.

42. A pharmaceutical composition comprising
(i) an ammonium salt of the compound of formula III:

(III)

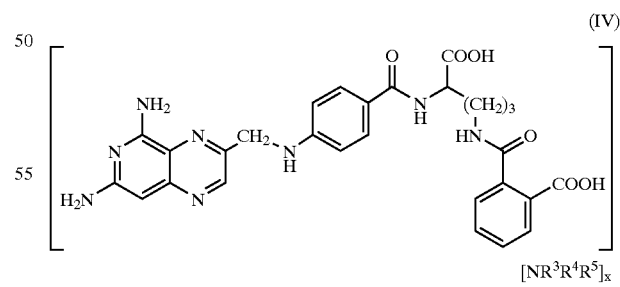

wherein:
R$^2$ represents up to four groups each independently selected at each occurrence of R$^2$ from the group consisting of hydrogen, C$_{1-6}$ alkyl, C$_{2-6}$ alkenyl, C$_{2-6}$ alkynyl, C$_{3-8}$ cycloalkyl, C$_{1-6}$ alkoxy, chloro, fluoro, hydroxy, and —COOH;

R$^3$, R$^4$, and R$^5$ are each independently selected from hydrogen and C$_{1-6}$ alkyl; or NR$^3$R$^4$ taken in combination form a 5 to 7 member heterocycle having at least one nitrogen ring atom; and x is a real number greater than 0 and less than about 4; and
(ii) a pharmaceutically acceptable carrier.

43. A pharmaceutical composition comprising
(i) an ammonium salt of the compound of formula IV:

(IV)

wherein:
R$^3$, R$^4$, and R$^5$ are each independently selected from hydrogen and C$_{1-6}$alkyl or NR$^3$R$^4$ taken in combination form a 5 to 7 member heterocycle having at least one nitrogen ring atom; and x is a real number greater than 0 and less than about 4; and (ii) a pharmaceutically acceptable carrier.

44. A pharmaceutical composition comprising
(i) an ammonium salt of the compound of formula V:

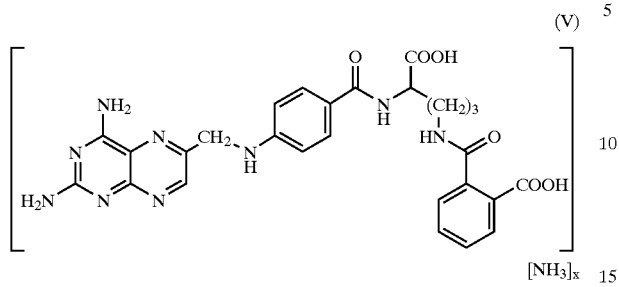

wherein x is a real number greater than 0 and less than about 4; and (ii) a pharmaceutically acceptable carrier.

45. The pharmaceutical composition of claim 41, wherein $NR^3R^4R^5$ represents ammonia, piperazinium, or 2-hydroxyethylammonium.

46. The pharmaceutical composition of claim 41, wherein $NR^3R^4R^5$ represents ammonia.

47. The pharmaceutical composition of claim 42, wherein $NR^3R^4R^5$ represents ammonia, piperazinium, or 2-hydroxyethylammonium.

48. The pharmaceutical composition of claim 47, wherein $NR^3R^4R^5$ represents ammonia.

49. The pharmaceutical composition of claim 48, wherein x is a real number between about 0.5 and 3.

50. The pharmaceutical composition of claim 49, wherein x is a real number between about 1 and about 2.

51. The pharmaceutical composition of claim 43, wherein $NR^3R^4R^5$ represents ammonia, piperazinium, or 2-hydroxyethylammonium.

52. The pharmaceutical composition of claim 51, wherein $NR^3R^4R^5$ represents ammonia.

53. The pharmaceutical composition of claim 52, wherein x is a real number between about 0.5 and 3.

54. The pharmaceutical composition of claim 53, wherein x is a real number between about 1 and about 2.

55. The pharmaceutical composition of claim 43, wherein the compound comprises at least about 5 equivalents of water.

56. The pharmaceutical composition of claim 55, wherein the water is present in an amount of from about 0.5 to about 5 equivalents.

57. The pharmaceutical composition of claim 44, wherein x is a real number between about 0.5 and 3.

58. The pharmaceutical composition of claim 57, wherein x is a real number between about 1 and about 2.

59. The pharmaceutical composition of claim 44, wherein the compound comprises at least about 5 equivalents of water.

60. The pharmaceutical composition of claim 59, wherein the water is present in an amount of from about 0.5 to about 5 equivalents.

61. A method of treating leukemia or cancer involving lymphoblasts in a mammal comprising administering to a mammal an effective amount of an ammonium salt of the compound of formula II:

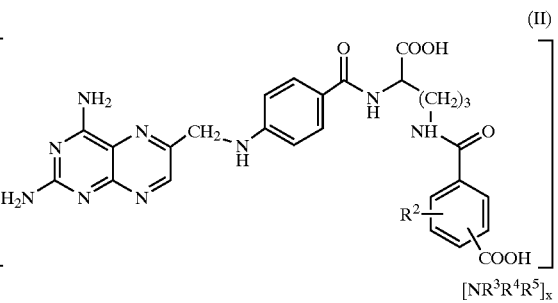

wherein:

$R^2$ represents up to four groups independently selected at each occurrence of $R^2$ from the group consisting of hydrogen, $C_{1-6}$ alkyl, $C_{2-6}$ alkenyl, $C_{2-6}$ alkynyl, $C_{3-8}$ cycloalkyl, $C_{1-6}$ alkoxy, chloro, fluoro, hydroxy, and —COOH;

$R^3$, $R^4$, and $R^5$ are each independently selected from hydrogen and $C_{1-6}$ alkyl; or $NR^3 R^4$ taken in combination can form a 5 to 7 member heterocycle having at least one nitrogen ring atom; and x is a real number greater than 0 and less than about 4.

62. The method of claim 61, wherein the mammal is a human.

63. A method of treating leukemia or cancer involving lymphoblasts in a mammal comprising administering to a mammal an effective amount of an ammonium salt of the compound of formula III:

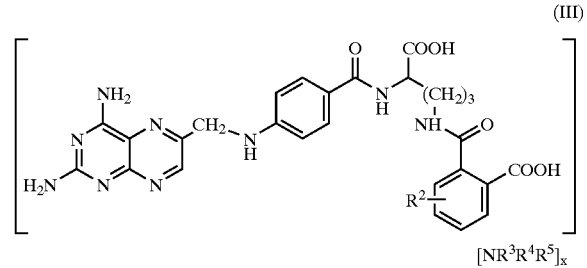

wherein:

$R^2$ represents up to four groups each independently selected at each occurrence of $R^2$ from the group consisting of hydrogen, $C_{1-6}$ alkyl, $C_{2-6}$ alkenyl, $C_{2-6}$ alkynyl, $C_{3-8}$ cycloalkyl, $C_{1-6}$ alkoxy, chloro, fluoro, hydroxy, and —COOH;

$R^3$, $R^4$, and $R^5$ are each independently selected from hydrogen and $C_{1-6}$ alkyl; or $NR^3R^4$ taken in combination form a 5 to 7 member heterocycle having at least one nitrogen ring atom; and x is a real number greater than 0 and less than about 4.

64. The method of claim 63, wherein the mammal is a human.

65. A method of treating leukemia or cancer involving lymphoblasts in a mammal comprising administering to a mammal an effective amount of an ammonium salt of the compound of formula IV:

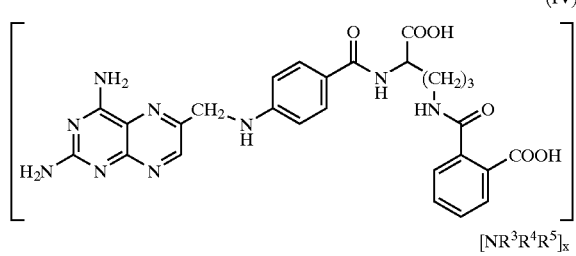

(IV)

wherein:

$R^3$, $R^4$, and $R^5$ are each independently selected from hydrogen and $C_{1-6}$alkyl or $NR^3R^4$ taken in combination form a 5 to 7 member heterocycle having at least one nitrogen ring atom; and x is a real number greater than 0 and less than about 4.

66. The method of claim 65, wherein the mammal is a human.

67. A method of treating leukemia or cancer involving lymphoblasts in a mammal comprising administering to a mammal an effective amount of an ammonium salt of the compound of formula V:

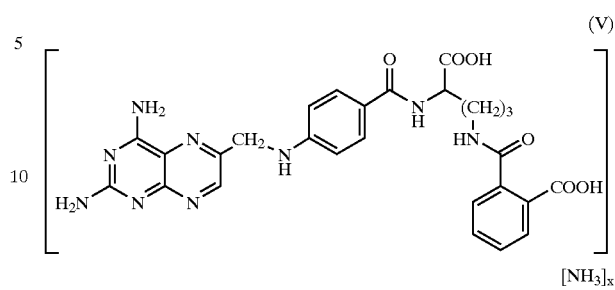

(V)

wherein x is a real number greater than 0 and less than about 4.

68. The method of claim 51, wherein the mammal is a human.

* * * * *